United States Patent
Takita et al.

(10) Patent No.: US 6,908,906 B2
(45) Date of Patent: Jun. 21, 2005

(54) CRYSTALLINE FORMS OF PYRIMIDINE NUCLEOSIDE DERIVATIVE

(75) Inventors: Takashi Takita, Hiratsuka (JP); Keiichi Ohtsuka, Sagamihara (JP); Eiji Numagami, Fujisawa (JP); Susumu Harashima, Yokohama (JP)

(73) Assignee: Sankyo Company, Limited, Tokyo (JP)

(*) Notice: Subject to any disclaimer, the term of this patent is extended or adjusted under 35 U.S.C. 154(b) by 0 days.

(21) Appl. No.: 10/637,300

(22) Filed: Aug. 7, 2003

(65) Prior Publication Data

US 2004/0053883 A1 Mar. 18, 2004

Related U.S. Application Data

(63) Continuation-in-part of application No. PCT/JP02/00986, filed on Feb. 6, 2002.

(30) Foreign Application Priority Data

Feb. 9, 2001 (JP) ........................................ 2001-033128

(51) Int. Cl.⁷ ..................... A61K 31/7068; C07H 19/06
(52) U.S. Cl. ......................... 514/49; 514/43; 536/28.5; 536/28.51
(58) Field of Search ................... 514/49; 536/28.5, 536/28.51

(56) References Cited

U.S. PATENT DOCUMENTS 5,691,319 A * 11/1997 Kaneko et al. ............... 514/49

FOREIGN PATENT DOCUMENTS

| EP | 0 536 936 A1 | 4/1993 |
|---|---|---|
| JP | 05-194497 | 8/1993 |
| JP | 2569251 B | 10/1996 |

OTHER PUBLICATIONS

English translation of International Preliminary Examination Report Form PCT/IPEA/409 in International Application No. PCT/JP02/00986.

* cited by examiner

Primary Examiner—James O. Wilson
Assistant Examiner—Michael C. Henry
(74) Attorney, Agent, or Firm—Frishauf, Holtz, Goodman & Chick, P.C.

(57) ABSTRACT

The present invention provides crystalline forms and compositions thereof, of a pyrimidine nucleoside derivative of formula (I) having anti-tumour activity, wherein formula (I) is:

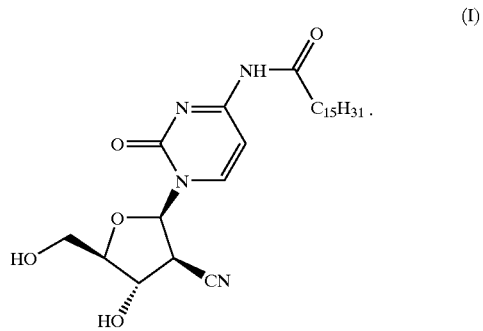

10 Claims, 4 Drawing Sheets

CRYSTALLINE FORMS OF PYRIMIDINE NUCLEOSIDE DERIVATIVE

This is a Continuation-in-Part Application of International Application No. PCT/JP02/00986 filed Feb. 6, 2002, incorporated herein by reference in its entirety.

BACKGROUND OF THE INVENTION

The present invention relates to crystalline forms of a pyrimidine nucleoside derivative which exhibit excellent anti-tumour activity; to a pharmaceutical composition (preferably an anti-tumour agent) containing said crystalline form as an active ingredient; to the use of said crystalline form in the preparation of said pharmaceutical composition; and to a method for prevention or treatment of disease (preferably tumour) which comprises administering to a warm blooded animal (preferably a human) in need of such prevention or treatment a pharmacologically effective amount of said crystalline form.

[Background of the Invention]

The pyrimidine nucleoside derivative of formula (I) (hereinafter referred to as Compound (I)) has been disclosed in Japanese Patent No. 2569251 and U.S. Pat. No. 5,691,319. As described therein, compound (I) exhibits excellent anti-tumour activity and is expected to become an agent for treatment or prevention of tumours. To make Compound (I) more practical for use as a medicament, better storage stability, ease of handling and the like is required.

BRIEF DESCRIPTIONS OF THE INVENTION

The inventors have studied the stability and the like of Compound (I) and have succeeded in obtaining crystals of Compound (I). These crystals have remarkably better storage stability and ease of handling than a powder of Compound (I) as obtained in example 1 disclosed in Japanese Patent No. 2569251 and U.S. Pat. No. 5,691,319. These crystals exhibit an excellent pharmacokinetic profile such as oral absorption and the like and are, therefore, practically useful medicaments as described in U.S. Pat. No. 5,691,319 (incorporated herein by reference).

Figure 1:
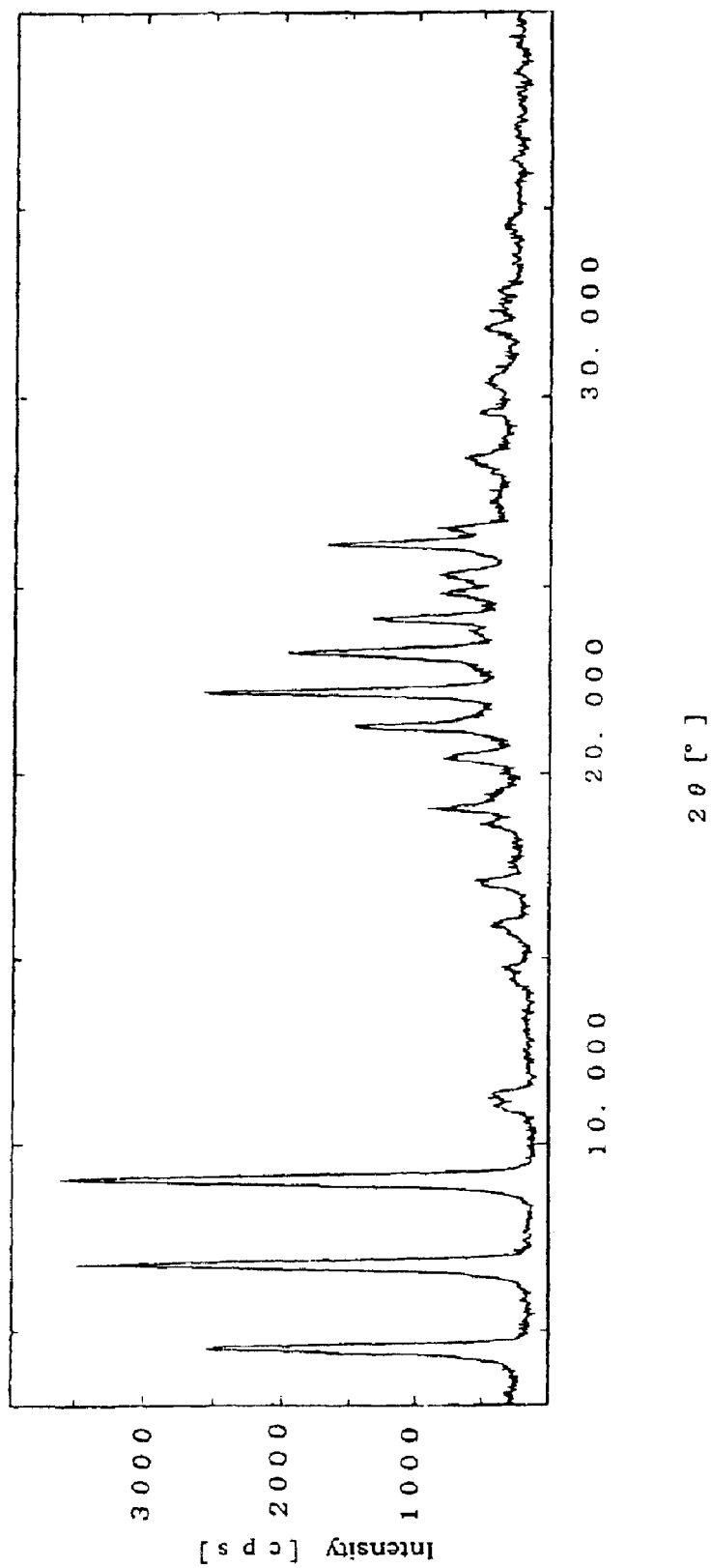
FIG. 1 is a powder X ray diffraction pattern of the crystalline product prepared in Example 1, the diffraction pattern of which is obtained by irradiation of the crystalline product using the copper Kα ray (wavelength λ=1.54 angstrom).
Figure 2:
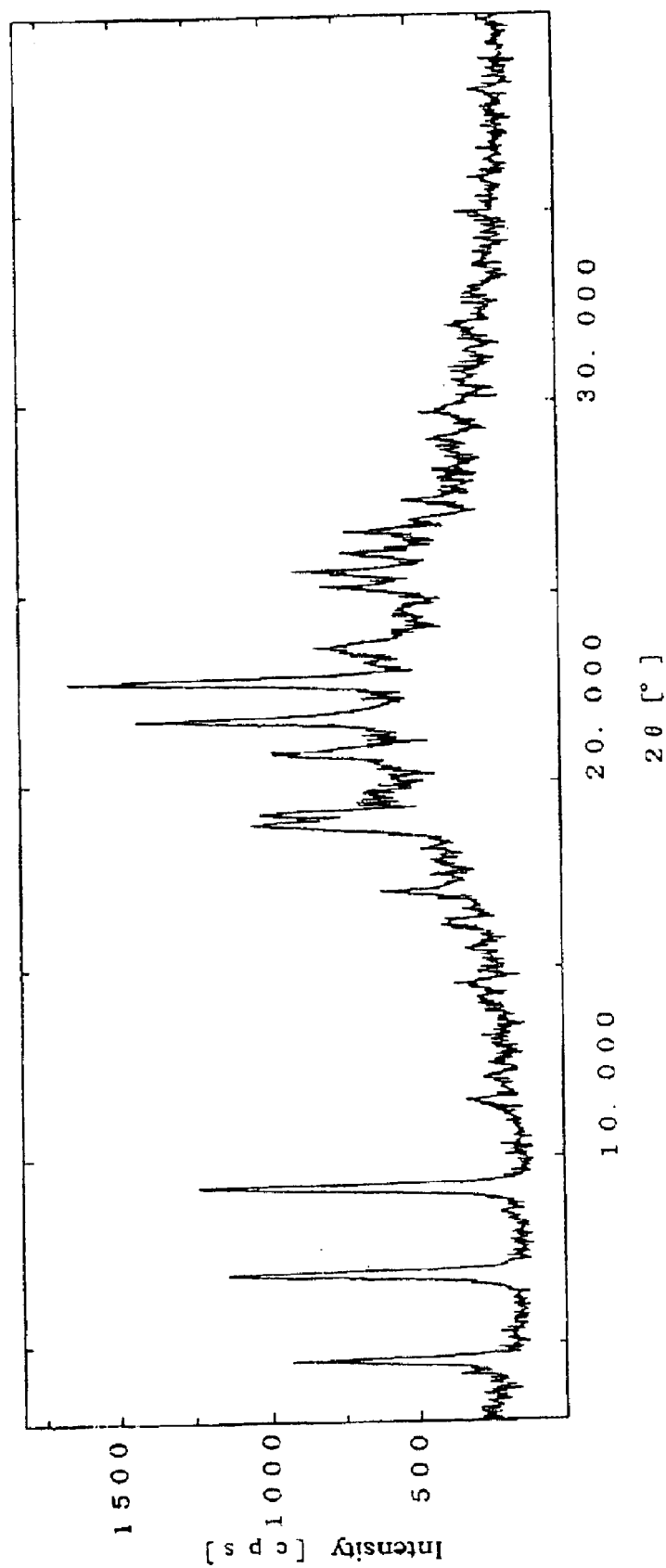
FIG. 2 is a powder X ray diffraction pattern of the crystalline product prepared in Example 2, the diffraction pattern of which is obtained by irradiation of the crystalline product using the copper Kα ray (wavelength λ=1.54 angstrom).
Figure 3:
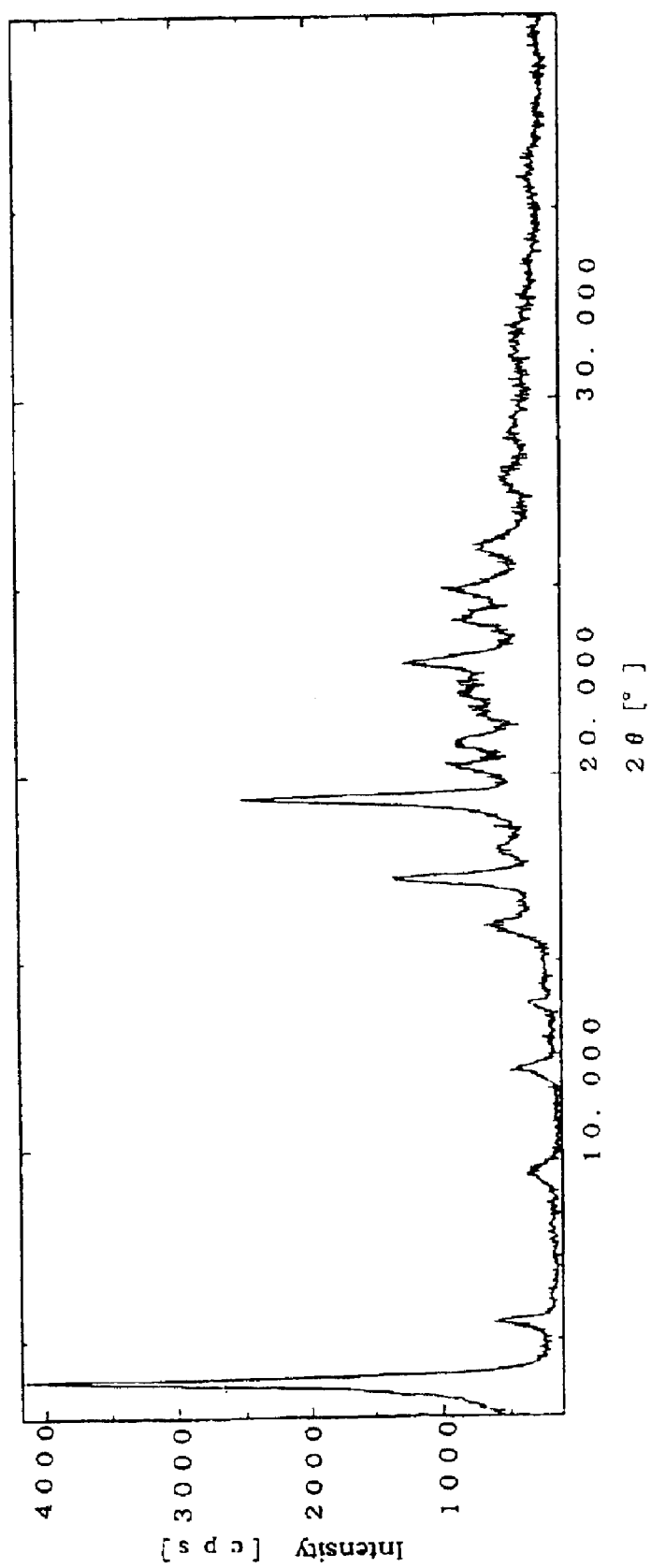
FIG. 3 is a powder X ray diffraction pattern of the crystalline product prepared in Example 3, the diffraction pattern of which is obtained by irradiation of the crystalline product using the copper Kα ray (wavelength λ=1.54 angstrom).
Figure 4:
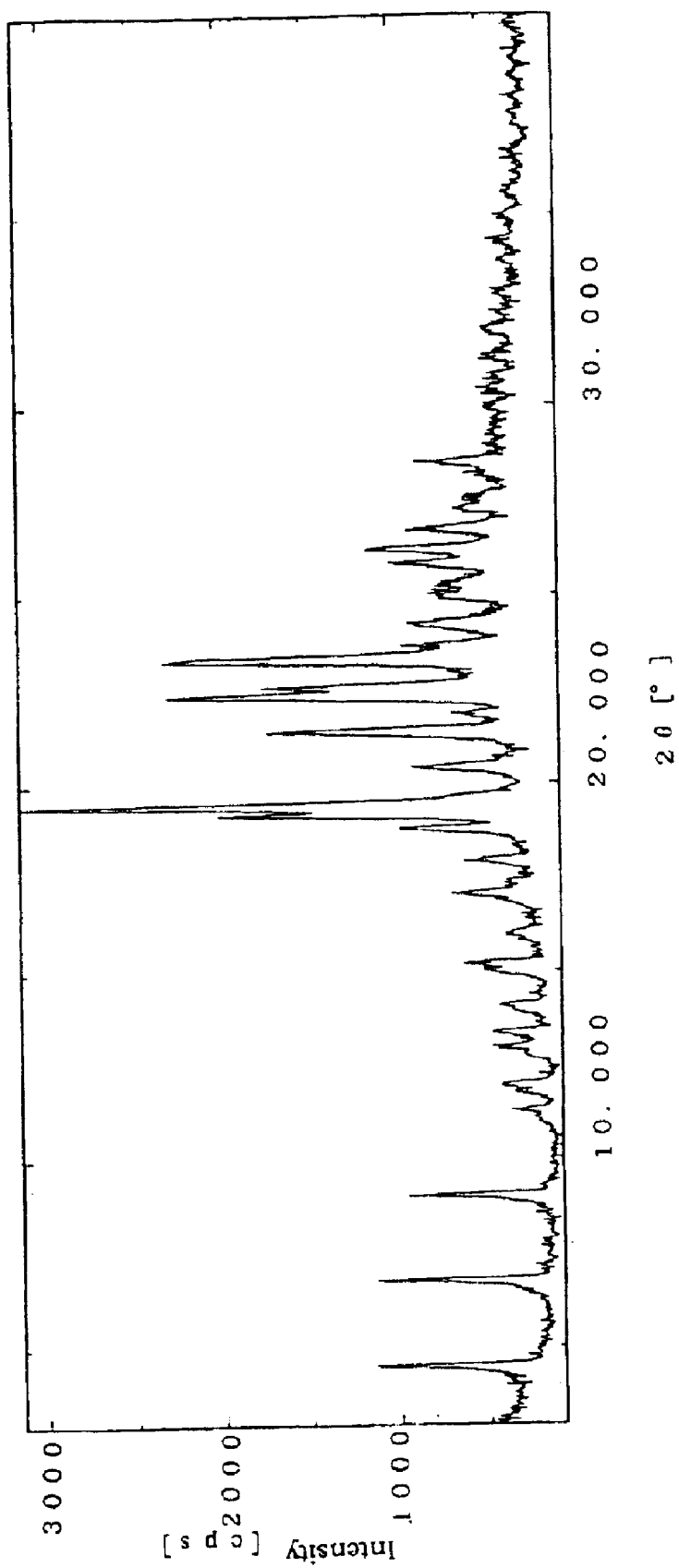
FIG. 4 is a powder X ray diffraction pattern of the crystalline product prepared in Example 4, the diffraction pattern of which is obtained by irradiation of the crystalline product using the copper Kα ray (wavelength λ=1.54 angstrom).

In addition, in these figures the vertical axis of each powder X ray diffraction pattern indicates the diffraction intensity in units of counts/second (cps) and the horizontal axis indicates the diffraction angle as the value 2θ.

DETAILED DESCRIPTION OF THE INVENTION

According to the invention there is provided:

(1) a crystalline form of a compound of formula (I):

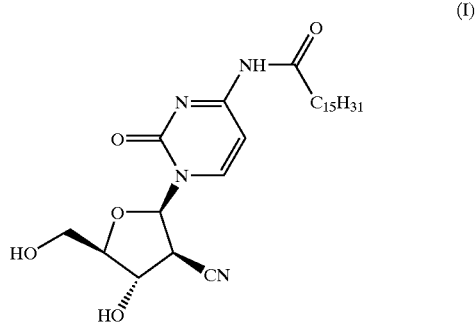

(2) a crystalline form according to (1) wherein the compound of formula (I) is a hydrate, (3) a crystalline form according to (1) or (2) wherein said crystalline form has main peaks at lattice distances of 19.53, 13.03, 9.75, 4.17, 4.00, 3.82, 3.68 and 3.41 angstroms determined by X-ray diffraction by the powder method using the copper Kα ray (wavelength λ=1.54 angstroms), (4) a crystalline form according to (1) or (2) wherein said crystalline form has main peaks at lattice distances of 19.36, 12.87, 9.63, 4.70, 4.64, 4.28, 4.10, 3.92, 3.77 and 3.48 angstroms determined by X-ray diffraction by the powder method using the copper Kα ray (wavelength λ=1.54 angstroms), (5) a crystalline form according to (1) or (2) wherein said crystalline form has main peaks at lattice distances of 19.62, 13.06, 9.82, 4.72, 4.63, 4.56, 4.15, 3.98, 3.93, 3.82, 3.45 and 3.40 angstroms determined by X-ray diffraction by the powder method using the copper Kα ray (wavelength λ=1.54 angstroms), (6) a crystalline form according to (1) or (2) wherein said crystalline form has peaks at lattice distances of 22.52, 5.17, 4.60, 4.28, and 3.87 angstroms determined by X-ray diffraction by the powder method using the copper Kα ray (wavelength λ=1.54 angstroms), (7) a pharmaceutical composition containing a crystalline form according to any one of (1) to (6) as an active ingredient, (8) a pharmaceutical composition according to (7) for prevention or treatment of tumours, (9) the use of a crystalline form according to any one of (1) to (6) in the preparation of a pharmaceutical composition,

(10) the use according to (9) wherein the pharmaceutical composition is for the prevention or treatment of tumours,

(11) a method for the prevention or treatment of disease comprising administering a pharmacologically effective amount of a crystalline form according to any one of (1) to (6) to a warm blooded animal in need of such prevention or treatment,

(12) a method according to (11) wherein the disease is a tumour,

(13) a method according to (11) or (12) wherein the warm blooded animal is a human.

The crystalline form of Compound (I) in the present invention is a solid which has a regular repeated arrangement of atoms (or groups of atoms) in a three-dimensional structure. The crystal is different from an amorphous solid that has no regular arrangement of atoms in a three-dimensional structure.

In general, different plural crystalline forms (polymorphism) of the same compound can be produced depending upon the crystallization conditions used. These different crystalline forms have different three-dimensional structures and have different physicochemical properties.

The present invention encompasses individual crystalline forms and mixtures of two or more of said crystalline forms.

Crystalline forms of Compound (I) include, for example:

a crystal having main peaks at lattice distances of d=19.53, 13.03, 9.75, 4.17, 4.00, 3.82, 3.68 and 3.41 angstrom determined by X-ray diffraction by the powder method using the copper K$\alpha$ a ray (wavelength $\lambda$=1.54 angstrom) wherein the main peaks have relative diffraction intensities greater than 36 based on the relative intensity 100 of the peak at lattice distance d=9.75 angstrom;

(In addition, the lattice distance d can be calculated on the basis of the equation of $2d \sin \theta = n\lambda$ (n=1).)

a crystal having main peaks at lattice distances of d=19.36, 12.87, 9.63, 4.70, 4.64, 4.28, 4.10, 3.92, 3.77 and 3.48 angstrom determined by X-ray diffraction by the powder method using the copper K$\alpha$ ray (wavelength $\lambda$=1.54 angstrom) wherein the main peaks have relative diffraction intensities greater than 53 based on the relative intensity 100 of the peak at lattice distance d=3.92 angstrom;

a crystal having main peaks at lattice distances of d=19.62, 13.06, 9.82, 4.72, 4.63, 4.56, 4.15, 3.98, 3.93, 3.82, 3.45 and 3.40 angstrom determined by X-ray diffraction by the powder method using the copper K$\alpha$ ray (wavelength $\lambda$=1.54 angstrom) wherein the main peaks have relative diffraction intensities greater than 30 based on the relative intensity 100 of the peak at lattice distance d=4.56 angstrom; and a crystal having peaks at lattice distances of d=22.52, 5.17, 4.60, 4.28, and 3.87 angstrom determined by X-ray diffraction by the powder method using the copper K$\alpha$ ray (wavelength $\lambda$=1.54 angstrom) wherein the main peaks have relative diffraction intensities greater than 36 based on the relative intensity 100 of the peak at lattice distance d=22.52 angstrom.

When the crystalline forms of Compound (I) are allowed to stand so that they are open to the atmosphere or are mixed with water or a solvent, they may absorb water or a solvent to form a hydrate or solvate. The present invention encompasses these hydrates and solvates The compound (I) can be prepared according to a similar procedure to that described in the specification of Japanese Patent No. 2569251 and in U.S. Pat. No. 5,691,319.

The crystalline forms of Compound (I) can be obtained from a supersaturated solution. The supersaturated solution can be prepared through dissolution of Compound (I) in an appropriate solvent, pH adjustment of said solution, concentration of said solution, cooling said solution, addition of a solvent in which Compound (I) is slightly soluble to a solution of Compound (I) in a solvent in which Compound (I) is readily soluble, or the like.

A suspension of a crystal or amorphous solid of Compound (I) in an appropriate solvent is converted into a slurry and then is stirred to transform alternate crystal (solvent-mediated transformation).

In addition, precipitation of the crystals takes place spontaneously in the reaction vessel or it can be started or accelerated by addition of a crystalline seed, by mechanical stimulation such as through use of ultrasonic waves or by stretching the inside of the reaction vessel.

The temperature for crystallization of Compound (I) or a pharmacologically acceptable salt thereof is usually in the range between 0 and 60° C., preferably between 5 and 45° C.

Precipitated crystals can be collected by filtration, centrifugation or decantation methods. Isolated crystals may be washed with an appropriate solvent. The washing solvent can include, for example, water; an alcohol such as ethanol, isopropanol; a ketone such as acetone; an ester such as methyl formate, ethyl formate, methyl acetate, ethyl acetate; an aromatic hydrocarbon such as toluene, xylene; a nitrile such as acetonitrile; an ether such as diethyl ether, tetrahydrofuran, or a mixture thereof. Preferably methyl acetate which contains water or is anhydrous is used.

Isolated crystals can be dried between 10 and 100° C., preferably between 30 and 50° C. until the weight of said crystals becomes constant, if necessary, in the presence of a drying agent such as silica gel or calcium chloride and under reduced pressure.

Dried crystals may absorb water under condition of 20 to 90% relative humidity and between 10 and 30° C., preferably 50 to 80% relative humidity and between 20 and 30° C. until the weight of said crystals becomes constant.

Crystals thus obtained can be further purified by recrystallization or slurry-purification.

The recrystallization is accomplished by techniques known to those skilled in the art such as (1) cooling method: Compound (I) or a pharmacologically acceptable salt is dissolved in a hot solvent and then the resulting solution is cooled, (2) concentration method: a solution of Compound (I) or a pharmacologically acceptable salt thereof is concentrated, (3) precipitation method: a solvent in which Compound (I) or a pharmacologically acceptable salt thereof is slightly soluble is added to a solution of Compound (I) or a pharmacologically acceptable salt thereof in a solvent in which Compound (I) or a pharmacologically acceptable salt is readily soluble.

The slurry-purification comprises collection of crystals which are obtained by stirring a suspension of a certain compound in an appropriate solvent.

The solvent employed in slurry-purification of Compound (I) includes, for example, a ketone such as acetone, methyl ethyl ketone; an ester such as methyl acetate, ethyl acetate; a nitrile such as acetonitrile; a halogenated hydrocarbon such as methylene chloride, chloroform; an aromatic hydrocarbon such as toluene, xylene; an alcohol such as ethanol, isopropanol; an ether such as diethyl ether, tetrahydrofuran; an amide such as N,N-dimethylformamide; water; an aliphatic hydrocarbon such as hexane; an ether such as diisopropyl ether, diethyl ether; or the like and a mixture thereof. Preferably a ketone such as acetone, methyl ethyl ketone; an ester such as methyl formate, ethyl formate, methyl acetate, ethyl acetate; a nitrile such as acetonitrile; an alcohol such as ethanol, isopropanol and these solvents containing water is used, and more preferably methyl acetate which contains water or is anhydrous.

Crystals obtained by recrystallization and slurry-purification are also isolated by similar techniques to those described hereinbefore.

When crystalline forms of Compound (I) are used as a medicament preferably as an agent for treatment or prevention of tumours (as described in U.S. Pat. No. 5,691,319), said crystalline forms can be administered alone or as a mixture of said crystalline form with an appropriate pharmacologically acceptable excipient(s), and/or diluent(s). Compositions according to the present invention can be in unit dosage form such as tablets, capsules, granules, powders, syrups, injections, ointments, solutions, suspensions, aerosols, troches or the like for oral or parenteral administration.

The pharmaceutical compositions can be prepared in a known manner by using additives such as excipients, binding agents, disintegrating agents, lubricating agents, stabilizing agents, corrigents, suspending agents, diluents and solvents.

An example of an excipient includes a sugar derivative such as lactose, sucrose, glucose, mannitol, or sorbitol; a starch derivative such as corn starch, potato starch, α-starch, dextrin, carboxy methylstarch; a cellulose derivative such as crystalline cellulose, low-substituted hydroxypropylcellulose, hydroxypropylmethylcellulose, carboxymethylcellulose, calcium carboxymethylcellulose, internal-cross-linked sodium carboxymethylcellulose; acacia; dextran; pullulan; a silicate derivative such as light silicic acid anhydride, synthetic aluminum silicate, magnesium aluminate metasilicate; a phosphate derivative such as calcium phosphate; a carbonate derivative such as calcium carbonate; a sulfate derivative such as calcium sulfate; or the like.

An example of a binding agent includes an excipient described hereinbefore; gelatin; polyvinylpyrrolidone; macrogol; or the like.

An example of a disintegrating agent includes an excipient described hereinbefore, a chemically modified starch or cellulose derivative such as sodium cross-carmellose, sodium carboxymethylstarch, cross-linked polyvinylpyrrolidone or the like.

An example of a lubricating agent includes talc; stearic acid; a metal stearate derivative such as calcium stearate, magnesium stearate; colloidal silica; veegum; a wax such as beeswax or spermaceti; boric acid; a glycol; a carboxy acid derivative such as fumaric acid, adipic acid; a sodium carboxylate such as sodium benzoate; a sulfate such as sodium sulfate; leucine; a lauryl sulfate such as sodium lauryl sulfate, or magnesium lauryl sulfate; a silicic acid derivative such as silicic acid anhydride, silicic acid hydrate; a starch derivative described above as an excipient; or the like.

An example of a stabilizing agent includes a para-hydroxybenzoic acid ester derivative such as methylparabene, propylparabene; an alcohol derivative such as chlorobutanol, benzyl alcohol, phenethyl alcohol; benzalkonium chloride; a phenol derivative such as phenol, cresol; thimerosal; acetic anhydride; sorbic acid; or the like.

An example of a corrigent includes a sweetening, souring, and flavoring agents or the like all of which are ordinarily used.

An example of a solvent includes water, ethanol, glycerin or the like.

The dose of the crystalline form of compound (I) will depend on such factors as symptom, body weight and age of the patient. A suitable dosage level for an adult human patient is 0.1 mg (preferably 1 mg) per day to 100 mg (preferably 50 mg) per day. The crystalline form of the compound of formula (I) can be administered as either a single unit dosage, or if desired, the dosage may be divided into convenient subunits administered at one to several times throughout the day depending on the symptoms of the patient.

EXAMPLES

The present invention is further described by Examples. Test examples and Formulation examples.

Example 1

Crystal B (a) To 2'-cyano-2'-deoxy-$N^4$-palmitoyl-1-β-D-arabinofuranosylcytosine (30 g), which is the compound described in Example 1 (1d) of the Japanese Patent No. 2569251 (or U.S. Pat. No. 5,691,319), was added methyl acetate containing water at 2.5 vol % (300 ml), and the resulting mixture was heated up to approximately 55° C. to prepare a clear solution. Subsequently, the solution was cooled to 5° C. at a rate of approximately 0.5° C. per minute. Upon cooling to about 45° C. in the course of the cooling, plate crystals were separated out of solution. After stirring furthermore at 5° C. for 20 min, the separated crystals were collected by filtration and washed with methyl acetate containing water at 2.5 vol % (30 ml) to afford the desired crystal B (28.78 g, purity 97.9%) in a 96.0% [N/N] yield.

(b) To 2'-cyano-2'-deoxy-$N^4$-palmitoyl-1-β-D-arabinofuranosylcytosine (8.7 kg), which is the compound described in Example 1 (1d) of the Japanese Patent No. 2569251 (or U.S. Pat. No. 5,691,319), was added methyl acetate containing water at 1.9 vol % (80 L), and the resulting mixture was stirred at approximately 23° C. for 1.5 hr. The separated crystals were collected by filtration, washed with methyl acetate containing water at 1.9 vol % (20 L) and dried to afford the desired crystal B (7.7 kg, purity 97.3%) in a 90.1% [N/N] yield.

Example 2

Crystal C (a) To 2'-cyano-2'-deoxy-$N^4$-palmitoyl-1-β-D-arabinofuranosylcytosine (30 g), which is the compound described in Example 1 (1d) of the Japanese Patent No. 2569251 (or U.S. Pat. No. 5,691,319), was added methyl acetate containing water at 4 vol % (600 ml), and the resulting mixture was heated up to approximately 50° C. to prepare a clear solution. Subsequently, the solution was cooled to 40° C. at a rate of approximately 0.5° C. per minute and stirred. In the course of the stirring, crystal B was first separated out of solution and then transformed gradually into needle-like crystals. After stirring furthermore at 40° C. for 60 min, the solution was cooled to 25° C. at a rate of approximately 0.5° C. per minute. After stirring at 25° C. for 60 min, the separated crystals were collected by filtration and washed with methyl acetate containing water at 4 vol % (30 ml) to afford the desired crystal C (23.74 g, purity 98.5%) in a 79.7% [N/N] yield.

(b) To 2'-cyano-2'-deoxy-$N^4$-palmitoyl-1-β-D-arabinofuranosylcytosine (60 g), which is the compound described in Example 1 (1d) of the Japanese Patent No. 2569251 (or U.S. Pat. No. 5,691,319), was added methyl acetate containing water at 2.5 vol %(600 ml), and the resulting mixture was stirred at about 23° C. for 2 hr and then cooled to 12° C. at a rate of approximately 0.5° C. per minute. After stirring at 12° C. for 1 hr, the separated crystals were collected by filtration, washed with methyl acetate containing water at 2.5 vol % (180 ml) and dried to afford the desired crystal C (55.1 g, purity 94.5%) in a 89.6% [N/N] yield.

Example 3

Crystal C(I)

1) The dried crystal C was kept standing for about 20 min under an atmosphere moistened to more than 45% humidity to afford the desired crystal C(I).

2) To the dried crystal C was added water to an amount which corresponds to about 33 wt % of the used crystal, and the resulting mixture was kneaded for 3 min to afford the desired crystal C(I).

Example 4

Crystal D (a) To 2'-cyano-2'-deoxy-$N^4$-palmitoyl-1-β-D-arabinofuranosylcytosine (10.0 g), which is the compound described in Example 1 (1d) of the Japanese Patent No. 2569251 (or U.S. Pat. No. 5,691,319), was added anhydrous methyl acetate (400 ml), and the resulting mixture was heated up to approximately 60° C. to prepare a clear solution. Subsequently, the solution was cooled to 25° C. at a rate of approximately 0.5° C. per minute. Upon cooling to about 43° C. in the course of the cooling, crystals were separated out of solution. After cooling to 25° C., the separated crystals were collected by filtration to afford the desired crystal D (8.8 g, 88.4% yield).

(b) To 2'-cyano-2'-deoxy-$N^4$-palmitoyl-1-β-D-arabinofuranosylcytosine (50 g), which is the compound described in Example 1 (1d) of the Japanese Patent No. 2569251 (or U.S. Pat. No. 5,691,319), was added methyl acetate (1500 ml), and the resulting mixture was heated up to approximately 50° C. and stirred at about 50° C. for 1 hr. Subsequently, the solution was cooled to 40° C. at a rate of approximately 0.5° C. per minute. After stirring at 40° C. for 30 min, the separated crystals were collected by filtration and dried to afford the desired crystal D (37.0 g, purity 99.2%) in a 74.2% [N/N] yield.

Test Example 1

Stability Test

In the stability test, crystals B, C and D of the present invention prepared in Examples 1, 2 and 4, respectively and the amorphous powder (Amorphous A) of compound of general formula (I) described in Example 1 (1d) of the Japanese Patent No. 2569251 were used as reference. These compounds were placed in stoppered vessels separately and stored at 60° C. under a nitrogen atmosphere for 17 days, and the content of these compounds was measured on 5, 10 and 17 days after the initiation of the storage.

The content of these compounds was determined quantitatively with high performance liquid chromatography (HPLC), and the rate of the remaining compounds (%) was calculated by the content of Compound (I) determined at each sampling point based on the initial content (100%) determined immediately before the storage.

The operating conditions of HPLC were as follows:

| Column: | L-column ODS (4.6 mm × 250 mm) (Chemicals Inspection and Testing Institute) |
|---|---|
| Mobile phase: | Acetonitrile:water:acetic acid = 750:250:1 |
| Flow rate: | 1.0 ml/min |
| Detection wavelength: | 249 nm |
| Column temperature: | 40° C. |

TABLE 1

Stability of each compound at 60° C, under a nitrogen atmosphere (Residual rate)

| Compound | Days after the initiation of stability test | | |
|---|---|---|---|
| | 5 days | 10 days | 17 days |
| Amorphous A | 92.7% | 78.6% | 62.5% |
| Crystal B prepared in Example 1 | 101.0% | 100.3% | 100.4% |
| Crystal C prepared in Example 2 | 101.0% | 100.4% | 100.1% |
| Crystal D prepared in Example 4 | 99.9% | 98.3% | 98.4% |

Based on the results summarized in Table 1, the stability of the amorphous powder (amorphous A) of compound (I) at 60° C. under a nitrogen atmosphere was extremely low, and the residual rate decreased to 62.5% after storage for 17 days. By contrast, the residual rates of crystals B and C prepared in Example 1 and 2, respectively, under the same storage conditions were 100% each and that of the crystal D prepared in Example 4 was 98.4%, demonstrating that the stability of crystals of the present invention is extremely high.

Formulation Example 1

Solution 1

A solution is prepared so that said solution contains the compound prepared in Example 1 (10%(W/W)), benzalkonium chloride (0.04%(W/W)), phenethyl alcohol (0.04% (W/W)) and purified water (89.56%(W/W)).

Formulation Example 2

Solution 2

A solution is prepared so that said solution contains the compound prepared in Example 1 (10%(W/W)), benzalkonium chloride (0.04%(W/W)), propylene glycol (30%(W/W)) and purified water (39.96%(W/W)).

Formulation Example 3

Powder

A powder is prepared so that said powder contains the compound prepared in Example 1 (40%(W/W)) and lactose (60%(W/W)).

Formulation Example 4

Aerosol

An aerosol is prepared so that said aerosol contains the compound prepared in Example 1 (10%(W/W)), lecithin (0.5%(W/W)), fulon 11 (34.5%(W/W)) and fulon 12 (55% (W/W)).

The crystalline forms of this invention have remarkably better storage stability and ease of handling than the amorphous powder of Compound (I). Said crystalline forms exhibit excellent metabolic disposition such as oral absorption and the like and are, therefore, useful medicaments (preferably as agents for treatment or prevention of tumours).

What is claimed is:

1. A crystalline form of a compound of formula (I):

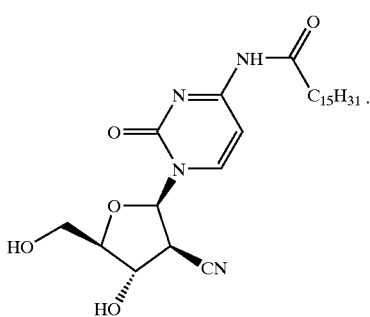

2. A crystalline form according to claim 1, wherein the compound of formula (I) is a hydrate.

3. A crystalline form according to claim 1 or claim 2, wherein said crystalline form has main peaks at lattice distances of 19.53, 13.03, 9.75, 4.17, 4.00, 3.82, 3.68 and 3.41 angstrom determined by X-ray diffraction by the powder method using the copper Kα ray (wavelength $\lambda=1.54$ angstrom).

4. A crystalline form according to claim 1 or claim 2, wherein said crystalline form has main peaks at lattice distances of 19.36, 12.87, 9.63, 4.70, 4.64, 4.28, 4.10, 3.92, 3.77 and 3.48 angstrom determined by X-ray diffraction by the powder method using the copper Kα ray (wavelength $\lambda=1.54$ angstrom).

5. A crystalline form according to claim 1 or claim 2, wherein said crystalline form has main peaks at lattice distances of 19.62, 13.06, 9.82, 4.72, 4.63, 4.56, 4.15, 3.98, 3.93, 3.82, 3.45 and 3.40 angstrom determined by X-ray diffraction by the powder method using the copper Kα ray (wavelength $\lambda=1.54$ angstrom).

6. A crystalline form according to claim 1 or claim 2, wherein said crystalline form has peaks at lattice distances of 22.52, 5.17, 4.60, 4.28, and 3.87 angstrom determined by X-ray diffraction by the powder method using the copper Kα ray (wavelength $\lambda=1.54$ angstrom).

7. A pharmaceutical composition containing an effective amount of a crystalline form according to claim 1 or claim 2 in a pharmaceutically acceptable additive.

8. A pharmaceutical composition according to claim 7, including additives suitable for administration for the treatment of tumors.

9. A method for the treatment of a tumor comprising administering a pharmacologically effective amount of a crystalline form according to claim 1 or claim 2 to a warm blooded animal in need of such treatment.

10. A method according to claim 9, wherein the warm blooded animal is a human.

* * * * *